(12) United States Patent
Akutsu

(10) Patent No.: US 9,016,131 B2
(45) Date of Patent: Apr. 28, 2015

(54) METHOD FOR DETECTING WAVELENGTH WITH SOUND PRESSURE SENSORS INSERTED IN A LIQUID

(75) Inventor: Shuichi Akutsu, Aikoh-gun (JP)

(73) Assignee: NHK Spring Co., Ltd., Kanagawa (JP)

( * ) Notice: Subject to any disclaimer, the term of this patent is extended or adjusted under 35 U.S.C. 154(b) by 883 days.

(21) Appl. No.: 13/198,908

(22) Filed: Aug. 5, 2011

(65) Prior Publication Data

US 2012/0060873 A1 Mar. 15, 2012

(30) Foreign Application Priority Data

Sep. 9, 2010 (JP) ................................ 2010-202043

(51) Int. Cl.
*G01N 29/032* (2006.01)
*G01N 29/265* (2006.01)
*B08B 3/12* (2006.01)
*B22D 11/16* (2006.01)
*G01N 29/22* (2006.01)
*G01N 29/44* (2006.01)

(52) U.S. Cl.
CPC ............ *G01N 29/032* (2013.01); *G01N 29/222* (2013.01); *G01N 29/265* (2013.01); *G01N 29/4436* (2013.01); *G01N 2291/02433* (2013.01)

(58) Field of Classification Search
CPC .............. G01N 29/032; G01N 29/222; G01N 29/4436; G01N 29/265; G01N 29/02
USPC ................ 134/184, 1.3; 73/649, 24.01, 61.75, 73/645, 646; 702/183
See application file for complete search history.

(56) References Cited

FOREIGN PATENT DOCUMENTS

JP          5-027256          3/1993

*Primary Examiner* — Helen Kwok
(74) *Attorney, Agent, or Firm* — Jordan and Hamburg LLP

(57) ABSTRACT

At least two sound pressure sensors in parallel with each other are inserted into a liquid to which waves are applied. The sound pressure sensors have a bar-like shape and the same sensitivity. In a first synchronized state waves detected by the sound pressure sensors are synchronized with each other. The sound pressure sensors are moved relative to each other in a longitudinal direction, to break the first synchronized state and then establish a second synchronized state in which the waves detected by the sound pressure sensors are again synchronized with each other. A wavelength of the detected waves is determined according to a quantity of the relative movement of the sound pressure sensors between the first and second synchronized states. The detection of a wavelength of waves applied to the liquid is usable to evaluate and control a total amount of dissolved gases in the liquid.

9 Claims, 2 Drawing Sheets

Total amount of dissolved gasses

METHOD FOR DETECTING WAVELENGTH WITH SOUND PRESSURE SENSORS INSERTED IN A LIQUID

BACKGROUND OF THE INVENTION

1. Field of the Invention

The present invention relates to a method of and an apparatus for detecting a wavelength in a liquid, a method of and an apparatus for evaluating a total amount of dissolved gases in a liquid, and a method of and an apparatus for controlling a total amount of dissolved gases in a liquid.

2. Description of Related Art

Ultrasonic cleaning gets a lot of attention and is widely used because it enhances a cleaning process, saves labor of the cleaning process, realizes high precision cleaning, secures uniformity of cleaning accuracy, and rationalizes cleaning work.

The ultrasonic cleaning creates cavitation in a cleaning liquid by ultrasonic waves and utilizes the cavitation as physical cleaning force. The magnitude of the cavitation is dependent on temperature and an amount of dissolved gases in the cleaning liquid. If the cleaning liquid contains a large amount of dissolved gases in form of, for example, bubbles, effect of the cavitation will deteriorate because the dissolved gases reflect ultrasonic waves.

To maintain accuracy of the ultrasonic cleaning, it is important that a total amount of dissolved gases in the cleaning liquid is evaluated. If the total amount of dissolved gases exceeds a predetermined or set value, the cleaning liquid must be degassed or replaced with new one.

It is relatively easy to measure an amount of dissolved oxygen. It is, however, very difficult to measure an amount of other dissolved gases such as carbon dioxide and it is impossible to evaluate a total amount of dissolved gases if the dissolved gases contain such unmeasurable gases.

To solve this problem, Japanese Unexamined Patent Application Publication No. H05-57256 discloses a dissolved gas concentration meter to measure an amount of dissolved gases such as nitrogen and carbon dioxide that are poorly reactive. The related art oppositely arranges first and second diaphragms and places an ultrasonic emitter made of a piezoelectric element on the first diaphragm and an ultrasonic sensor made of an ultrasonic wave strength measuring piezoelectric element on the second diaphragm.

The ultrasonic emitter emits ultrasonic waves and the ultrasonic sensor detects a value corresponding to a sound pressure of the ultrasonic waves. According to the detected value and a graph that relates the sound pressure corresponding value to an amount of dissolved gases, the related art measures an amount of dissolved gases.

It is unclear, however, if the related art is capable of measuring a total amount of a mixture of several kinds of gases because the relational graph used by the related art only refers to nitrogen gas.

Namely, the related art has not yet led to evaluate and control a total amount of dissolved gases in a liquid.

In the meantime, it is known that in ideal water at 25° C., the velocity of ultrasonic waves (sonic velocity) is 1496 m/sec. If there are bubbles of about 4 ppm in the water, the sonic velocity decreases to about 1000 m/sec.

Such decrease of ultrasonic wave due to bubbles is mentioned in J. Saneyoshi, Bulletin of Tokyo Institute of Technology, Series B, 1953, No. 1, p. 1 and A. Mallock, Proc. Roy. Soc. London, 84, p. 391 (1911). When the velocity of ultrasonic waves changes, the frequency of the ultrasonic waves is unchanged but the wavelength thereof changes. Accordingly, detecting a change in the wavelength of ultrasonic waves may be useful to find a change in dissolved gases (bubbles) in a liquid.

It is difficult, however, to detect a wavelength in a liquid as an indication of dissolved gases (bubbles).

SUMMARY OF THE INVENTION

An object of the present invention is to detect a wavelength in a liquid. An another object of the present invention is to, based on the detected wavelength, evaluate and control a total amount of dissolved gases in the liquid.

In order to accomplish the objects, a first aspect of the present invention provides a method of detecting a wavelength, including steps of inserting at least two sound pressure sensors in parallel with each other into a liquid to which waves are applied, the sound pressure sensors formed into a bar-like shape and having the same sensitivity, establishing a first synchronized state in which waves detected by the sound pressure sensors are synchronized with each other, moving the sound pressure sensors relative to each other in a longitudinal direction, to break the first synchronized state and then establish a second synchronized state in which waves detected by the sound pressure sensors are again synchronized with each other, and detecting a wavelength of the detected waves according to a quantity of the relative movement of the sound pressure sensors between the first and second synchronized states.

According to the first aspect, a wavelength of the detected waves is easily measured only by measuring a quantity of relative movement of the sound pressure sensors in a longitudinal direction.

A second aspect of the present invention provides a wavelength detecting apparatus for carrying out the method of the first aspect. The apparatus includes the at least two sound pressure sensors formed into a bar-like shape and having the same sensitivity and a display unit connected to the sound pressure sensors and simultaneously displaying waves detected by the sound pressure sensors on a time axis to allow the first and second synchronized states to be confirmed on the display unit.

According to the second aspect, the first and second synchronized states are confirmed on the display unit and a wavelength of the detected waves is easily measured only by measuring a quantity of relative movement of the sound pressure sensors in a longitudinal direction.

A third aspect of the present invention provides a method of evaluating a total amount of dissolved gases with use of the method of the first aspect. The method of the third aspect includes a step of, after carrying out the method of the first aspect, evaluating a total amount of dissolved gases in the liquid according to the detected wavelength and a preliminarily obtained relationship between wavelengths and dissolved gas quantities.

According to the third aspect, it realizes to evaluate the total amount of dissolved gases in the liquid.

A fourth aspect of the present invention provides a dissolved gas total amount evaluating apparatus for carrying out the method of the third aspect. The apparatus includes a cleaning tank containing the liquid and having an ultrasonic oscillator to apply ultrasonic waves to the liquid and clean an object immersed in the liquid, the at least two sound pressure sensors formed into a bar-like shape and having the same sensitivity, a display unit connected to the sound pressure sensors and simultaneously displaying waves detected by the sound pressure sensors on a time axis to allow the first and second synchronized states to be confirmed on the display unit, so that a total amount of dissolved gases in the liquid is evaluated by the relationship between wavelengths and dissolved gas quantities.

According to the fourth aspect, ultrasonic cleaning of the object is carried out in the cleaning tank. Moreover, the first and second synchronized states are confirmed on the display unit and a total amount of dissolved gases in the liquid is evaluated by measuring a quantity of relative movement of the sound pressure sensors in a longitudinal direction between the first and second synchronized states. With this, the liquid is properly managed.

A fifth aspect of the present invention provides a method of controlling a total amount of dissolved gases with use of the method of the third aspect. The method of the fifth aspect includes a step of, after carrying out the method of the third aspect, carrying out the method of the third aspect and degassing the liquid according to the total amount of dissolved gases until the evaluated total amount of dissolved gases decreases below a set value.

According to the fifth aspect, a total amount of dissolved gases in the liquid is easily controlled according to an evaluated amount of dissolved gases in the liquid.

A sixth aspect of the present invention provides an apparatus for controlling a total amount of dissolved gases. The apparatus includes the apparatus of the fourth aspect and further includes a degassing unit circulating and degassing the liquid according to the evaluated total amount of dissolved gases until the evaluated total amount of dissolved gases decreases below a set value.

According to the sixth aspect, the degassing unit easily controls a total amount of dissolved gases in the liquid according to an evaluated amount of dissolved gases.

DETAILED DESCRIPTION OF EMBODIMENTS

An embodiment of the present invention will be explained with reference to the drawings. The embodiment employs sound pressure sensors in order to detect a wavelength of ultrasonic waves in a liquid, and according to the detected wavelength, evaluates and controls a total amount of dissolved gases in the liquid.

Figure 1:
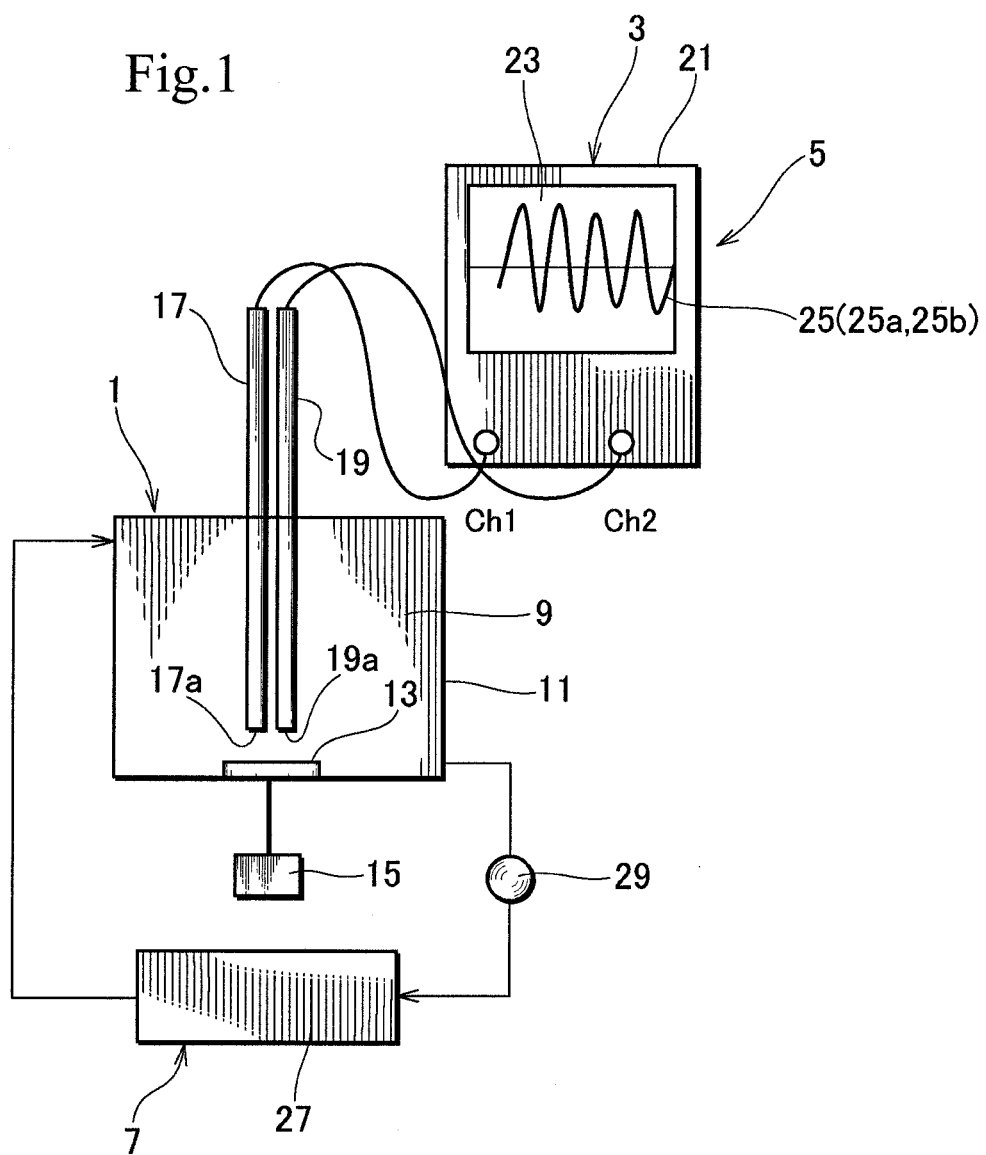
FIG. 1 is a schematic view illustrating an ultrasonic cleaning apparatus with a wavelength detector and the like according to an embodiment of the present invention.

FIG. 1 is a schematic view illustrating an ultrasonic cleaning apparatus. In FIG. 1, an ultrasonic cleaning apparatus 1 has a wavelength detector 3, a dissolved gas total amount evaluator 5, and a dissolved gas total amount controller 7.

The ultrasonic cleaning apparatus 1 includes a cleaning tank 11 containing a cleaning liquid 9 such as pure water and an ultrasonic oscillator 13 arranged on the bottom of the cleaning tank 11. The ultrasonic oscillator 13 is connected to an ultrasonic controller 15 that controls the frequency of ultrasonic waves generated by the ultrasonic oscillator 13 in the cleaning tank 11.

An object to be cleaned is immersed in the cleaning liquid 9 in the cleaning tank 11 and the ultrasonic oscillator 13 is activated to generate ultrasonic waves to clean the object. The cleaning operation is carried out according to, for example, a batch process.

The object to be cleaned by the ultrasonic cleaning apparatus 1 is, for example, a head suspension or a head gimbal assembly to be installed in a hard disk drive. The object may be a half-finished head suspension or other object cleanable by ultrasonic cleaning.

As the cleaning operation progresses, gases such as air, oxygen, nitrogen, and carbon dioxide dissolve in the cleaning liquid 9. An increase in the total amount of the dissolved gases results in deteriorating the cleaning accuracy of the object. To maintain the cleaning accuracy, the total amount of the dissolved gases must be evaluated, first. If the total amount exceeds a predetermined or set value, the cleaning liquid 9 must be degassed or replaced with new one whose total amount of dissolved gases is lower than a specified value.

When gases such as air dissolve in the cleaning liquid 9, bubbles occur in the cleaning liquid 9 to attenuate the velocity of ultrasonic waves in the cleaning liquid 9, as mentioned above. Even if the velocity attenuates, the frequency of the ultrasonic waves is unchanged. The wavelength of the ultrasonic waves, however, changes depending on the change in the velocity. Accordingly, detecting a change in the wavelength of ultrasonic waves will lead to detect a level of bubbles in the cleaning liquid 9.

Then, the ultrasonic cleaning apparatus 1 has the wavelength detector 3 as the foundation in addition to the cleaning tank 11 and the ultrasonic oscillator 13 as the basic structure for the ultrasonic cleaning.

The wavelength detector 3 is the apparatus to embody a method of detecting a wavelength of ultrasonic waves. Namely, the wavelength detector 3 has at least two sound pressure sensors 17 and 19 that are formed into a bar-like shape and have the same sensitivity. According to this embodiment, the sensors 17 and 19 have the same bar-like shape. Instead, the sensors 17 and 19 may have different bar-like shapes as long as they have the same sensitivity. The sensors 17 and 19 are connected to channels Ch1 and Ch2 of a display unit 21, respectively. The display unit 21 has a display panel 23 to simultaneously display detected waves, which are detected by the sensors 17 and 19, on a time axis so that an operator may confirm first and second synchronized states. The first and second synchronized states will be explained later.

Operation of the wavelength detector 3 will be explained with also reference to FIG. 2 that is a schematic view illustrating sound pressure sensors of the wavelength detector moved relative to each other in a longitudinal direction. As illustrated in FIG. 1, the sound pressure sensors 17 and 19 are inserted in parallel with each other into the cleaning liquid 9 in the cleaning tank 11 from above. In the cleaning liquid 9, front ends 17a and 19a of the sensors 17 and 19 are aligned with each other at the same level.

The ultrasonic controller 15 activates the ultrasonic oscillator 13 to generate ultrasonic waves. The ultrasonic waves are detected by the sound pressure sensors 17 and 19 and the detected waves 25 (25a, 25b) are displayed on the display panel 23 in an overlapped state.

If rise times of the detected waves 25a and 25b on the display panel 23 disagree with each other, the sensors 17 and 19 are finely moved relative to each other in a longitudinal direction, to make the detected waves 25a and 25b completely overlap each other. According to the embodiment illustrated in FIG. 1, the sensor 17 is translated relative to the sensor 19 so that rise times of the detected waves 25a and 25b agree with each other.

With this agreement, the detected waves 25a and 25b are synchronized with each other, i.e., they overlap each other on the display panel 23 to establish the first synchronized state.

Figure 2:
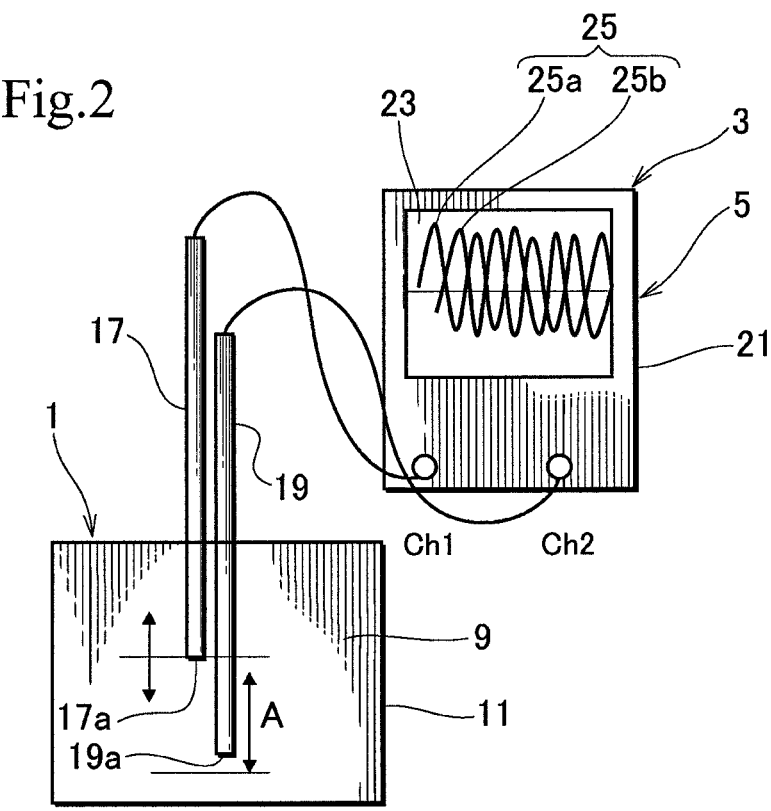
FIG. 2 is a schematic view illustrating sound pressure sensors of the wavelength detector moved relative to each other in a longitudinal direction.

From the first synchronized state, the sensors 17 and 19 are relatively moved in a longitudinal direction as illustrated in FIG. 2. According to the embodiment of FIG. 2, the sensor 17 is upwardly translated relative to the sensor 19.

Due to this translation, the detected waves 25a and 25b on the display panel 23 deviate from each other to break the first synchronized state and again agree with each other to establish the second synchronized state. At this time, a distance A between the front ends 17a and 19a of the sensors 17 and 19 is measured. According to the distance A, a wavelength of the detected waves 25a and 25b is found.

The distance A between the front ends 17a and 19a of the sensors 17 and 19 may be a distance between marks put at longitudinal centers or other longitudinally corresponding points of the sensors 17 and 19, respectively. In the measurement of the distance A, a measuring jig may be used to relatively move the sensors 17 and 19. The measurement can be realized by a human work, or a known information processor or controller such as a computer controlling the jig. In any case, the distance A is the wavelength of the detected waves 25a and 25b.

Figure 3:
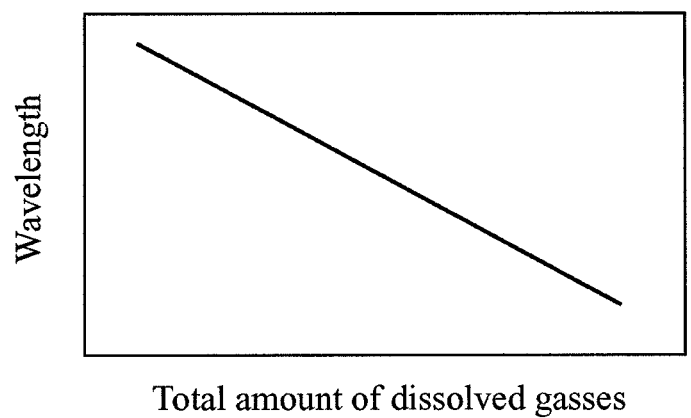
FIG. 3 is a graph illustrating a relationship between wavelength and amount of dissolved gases.

The dissolved gas total amount evaluator 5 will be explained with also reference to FIG. 3 that is a graph illustrating a relationship between wavelength and amount of dissolved gases.

The dissolved gas total amount evaluator 5 is provided for the ultrasonic cleaning apparatus 1 to carry out a method of evaluating a total amount of dissolve gases. The evaluator 5 is the combination of the cleaning tank 11, the sound pressure sensors 17 and 19, and the display unit 21. The evaluator 5 uses the combination as mentioned above to detect a wavelength of ultrasonic waves generated by the ultrasonic oscillator 13 in the cleaning liquid 9. According to the detected wavelength, the evaluator 5 refers to a relationship between ultrasonic wavelength and dissolved gas total amount illustrated in FIG. 3 that is prepared in advance, to evaluate a total amount of dissolved gases in the cleaning liquid 9. This evaluation can be realized by a comparison with a known information processor or controller such as a computer or a human work without an information processor or the like.

For example, the frequency of the ultrasonic waves generated by the ultrasonic oscillator 13 and applied to the cleaning liquid 9 is 132 kHz. If the velocity of the ultrasonic waves at the frequency of 132 kHz attenuates from 1500 msec to 1000 m/sec, the wavelength of the ultrasonic waves changes from 11.3 mm to 7.6 mm. Namely, a change in the wavelength is 3.7 mm. In connection with this, the distance A between the front ends 17a and 19a of the sensors 17 and 19 is measured with, for example, slide calipers in units of 1/10 millimeters. The longer the distance A, the smaller the total amount of dissolved gases.

The dissolved gas total amount controller 7 is provided for the ultrasonic cleaning apparatus 1 to carry out a method of controlling a total amount of dissolved gases. The controller 7 has a degasifier 27 and a pump 29 as a degassing unit in addition to the evaluator 5. The pump 29 circulates the cleaning liquid 9 through a circuit and the degasifier 27 is interposed the circuit to degas the circulated cleaning liquid 9. The degassing operation is carried out according to a result of evaluation made by the evaluator 5 until the total amount of dissolved gases in the cleaning liquid 9 decreases below a set value. A configuration of the degasifier 27 is explained in, for example, Japanese Unexamined Patent Application Publication No. H05-57256.

Operation of the ultrasonic cleaning apparatus 1 with the wavelength detector 3, dissolved gas total amount evaluator 5, and dissolved gas total amount controller 7 will be explained.

An object to be cleaned such as a head suspension is immersed in the cleaning liquid 9 in the cleaning tank 11. The ultrasonic controller 15 activates the ultrasonic oscillator 13 to generate ultrasonic waves. The ultrasonic waves cause cavitation to clean the object. These steps are carried out according to a batch process. During the process, the sensors 17 and 19 are placed outside the cleaning liquid 9.

As the cleaning operation progresses, gases such as air, oxygen, nitrogen, and carbon dioxide dissolve in the cleaning liquid 9, to deteriorate the cleaning power of the ultrasonic cleaning.

Then, the sensors 17 and 19 are inserted in parallel with each other into the cleaning liquid 9 from above the cleaning tank 11. The wavelength detector 3 with the display unit 21 detects and displays detected waves 25a and 25b. According to the first and second synchronized states of the detected waves 25a and 25b, a distance A between the front ends 17a and 19a of the sensors 17 and 19 is measured as mentioned above. Based on the distance A and the relationship of FIG. 3, a total amount of the dissolved gases is evaluated.

If the total amount is above a set value, the pump 29 is driven to circulate the cleaning liquid 9 and the degasifier 27 is operated to degas the circulated cleaning liquid 9 until the total amount of dissolved gases in the cleaning liquid 9 decreases below a set value.

As mentioned above, the embodiment of the present invention employs the at least two sound pressure sensors 17 and 19 that are formed into a bar-like shape and have the same sensitivity. The sensors 17 and 19 are inserted in parallel with each other into the cleaning liquid 9, to detect ultrasonic waves 25a and 25b. The detected waves 25a and 25b are displayed and confirmed on the display unit 21.

The sensors 17 and 19 are moved relative to each other so that the detected waves 25a and 25b establish a first synchronized state. From the first synchronized state, the sensors 17 and 19 are moved relative to each other to establish a second synchronized state. Based on the first and second synchronized states, a distance A between the front ends 17a and 19a of the sensors 17 and 19 is measured. According to the distance A, a wavelength of the detected waves 25a and 25b is found.

The wavelength of the detected ultrasonic waves is easily found only by measuring the distance A of relative longitudinal movement of the sensors 17 and 19.

According to the distance A and the prepared graph or relationship of wavelength and total amount of dissolved gases (FIG. 3), a total amount of dissolved gases in the cleaning liquid 9 is evaluated.

If the total amount of dissolved gases in the cleaning liquid 9 is above a set value, the pump 29 and degasifier 27 are operated to degas the cleaning liquid 9 until the total amount of dissolved gases in the cleaning liquid 9 decreases below a set value.

In this way, the present invention is capable of easily controlling a total amount of dissolved gases in the liquid 9 according to the evaluation of the total amount of dissolved gases.

The wavelength detector 3, dissolved gas total amount evaluator 5, and dissolved gas total amount controller 7 may be unified together through at least one controller realized by a computer. In this case, the sensors 17 and 19 are periodically inserted into the cleaning liquid 9 with a jig and components as the wavelength detector 3 electrically detect the distance A each time. The electrically detected distance A is sent to the controller storing the relationship of FIG. 3 and components as the evaluator 5 evaluate a total amount of dissolved gases. Based on a result of the evaluation, the controller instructs components as the controller 7 to drive the pump 29 and degasifier 27, thereby automatically degassing the cleaning liquid 9. During the degassing operation, the distance A is automatically and periodically measured, and if the distance A decreases to a specified value, the pump 29 and degasifier 27 are stopped.

What is claimed is:

1. A method of detecting a wavelength, comprising steps of:
    inserting at least two sound pressure sensors in parallel with each other into a liquid to which waves are applied, the sound pressure sensors having a bar-like shape and having the same sensitivity;
    establishing a first synchronized state in which waves detected by the sound pressure sensors are synchronized with each other;
    moving the sound pressure sensors relative to each other in a longitudinal direction, to break the first synchronized state and then establish a second synchronized state in which waves detected by the sound pressure sensors are again synchronized with each other; and
    detecting a wavelength of the detected waves according to a distance of the relative movement of the sound pressure sensors between the first and second synchronized states.

2. The method of claim 1, further comprising a step of:
    finely moving the sound pressure sensors relative to each other in the longitudinal direction until the first synchronized state is established if the waves detected after the insertion of the sound pressure sensors into the liquid are asynchronous with each other.

3. The method of claim 1, wherein the distance to provide proper antecedent basis of the relative movement of the sound pressure sensors is a distance between front ends of the sound pressure sensors in the longitudinal direction.

4. A wavelength detecting apparatus for carrying out the method of claim 1, comprising:
    the at least two sound pressure sensors having a bar-like shape and having the same sensitivity; and
    a display unit connected to the sound pressure sensors and simultaneously displaying waves detected by the sound pressure sensors on a time axis to allow the first and second synchronized states to be confirmed on the display unit.

5. A method of evaluating a total amount of dissolved gases with use of the method of claim 1, comprising a step of:
    evaluating a total amount of dissolved gases in the liquid according to the detected wavelength and a preliminarily obtained relationship between wavelengths and dissolved gas quantities after the wavelength detecting step.

6. A dissolved gas total amount evaluating apparatus for carrying out the method of claim 5, comprising:
    a cleaning tank containing the liquid and having an ultrasonic oscillator to apply ultrasonic waves to the liquid and clean an object immersed in the liquid;
    the at least two sound pressure sensors formed into a bar-like shape and having the same sensitivity;
    a display unit connected to the sound pressure sensors and simultaneously displaying waves detected by the sound pressure sensors on a time axis to allow the first and second synchronized states to be confirmed on the display unit, so that a total amount of dissolved gases in the liquid is evaluated by the relationship between wavelengths and dissolved gas quantities.

7. A method of controlling a total amount of dissolved gases with use of the method of claim 5, comprising a step of:
    degassing the liquid according to the evaluated total amount of dissolved gases until the total amount of dissolved gases in the liquid decreases below a set value after the evaluating step.

8. An apparatus for controlling a total amount of dissolved gases comprising the dissolved gas total amount evaluating apparatus of claim 6, the apparatus further comprising:
    a degassing unit circulating and degassing the liquid according to the evaluated total amount of dissolved gases until the total amount of dissolved gases in the liquid decreases below a set value.

9. The apparatus of claim 6, wherein the object to be cleaned is one of a head suspension and a head gimbal assembly used for a hard disk drive.

* * * * *

UNITED STATES PATENT AND TRADEMARK OFFICE
CERTIFICATE OF CORRECTION

| | |
|---|---|
| PATENT NO. | : 9,016,131 B2 |
| APPLICATION NO. | : 13/198908 |
| DATED | : April 28, 2015 |
| INVENTOR(S) | : Akutsu |

It is certified that error appears in the above-identified patent and that said Letters Patent is hereby corrected as shown below:

In the claims

Claim 3, Column 7, lines 36-37:

DELETE

"3. The method claim 1, wherein the distance to provide proper antecedent basis of the relative movement of the sound pressure sensors is a distance between front ends of the sound pressure sensors in the longitudinal direction."

and INSERT

--3. The method claim 1, wherein the distance of the relative movement of the sound pressure sensors is a distance between front ends of the sound pressure sensors in the longitudinal direction.--

Signed and Sealed this
Twenty-ninth Day of December, 2015

Michelle K. Lee
*Director of the United States Patent and Trademark Office*